United States Patent [19]
Wehrli

[11] Patent Number: 4,938,762
[45] Date of Patent: Jul. 3, 1990

[54] REFERENCE SYSTEM FOR IMPLANTATION OF CONDYLAR TOTAL KNEE PROSTHESES

[75] Inventor: Ulrich Wehrli, Wabern, Switzerland
[73] Assignee: Protek AG, Bern, Switzerland
[21] Appl. No.: 281,676
[22] Filed: Dec. 8, 1988

[30] Foreign Application Priority Data

Dec. 16, 1987 [CH] Switzerland .................. 4904/87

[51] Int. Cl.⁵ ............................................. A61F 5/04
[52] U.S. Cl. ................................................. 606/88
[58] Field of Search ...................... 606/88; 623/18, 39

[56] References Cited

U.S. PATENT DOCUMENTS

| | | | |
|---|---|---|---|
| 4,487,203 | 12/1984 | Androphy | 606/88 |
| 4,524,766 | 6/1985 | Petersen | 606/88 |
| 4,566,448 | 1/1986 | Rohr, Jr. | 606/88 |
| 4,567,885 | 2/1986 | Androphy | 606/88 |
| 4,567,886 | 2/1986 | Petersen | 606/88 |
| 4,574,794 | 3/1986 | Cooke et al. | 606/88 |

OTHER PUBLICATIONS

*Clinical Orthopaedics and Related Research*, No. 173, Mar. 1983, pp. 178-183, Bargren, J. H. et al., "Alignment in Total Knee Arthroplasty".
"Immediate Interlock Without Cement—The TRICON-P ™ Cementless Tibial Component with FLEX-LOK ™ Pegs", Richards Medical Company, 1983.
*Bio-Medical Engineering Corp. Technical Report*, 3/1983, Pappas, M. J. et al., "N.J. Knee Instrumentation System: Biomechanical and Surgical Rationale".
"Surgical Technique Using AOR ™ Total Knee Instrumentation for the Miller/Galante Porous Tivanium Total Knee System", Zimmer, undated, pp. 8 & 18-20.
"The Intermedics Natural-Knee ™ System—Instrumentation", Intermedics Orthopedics, 1986.
"Precise Bone Cuts . . . Every Time—The Howmedical Universal Total Knee Instrument System", Howmedical, Inc., 1980 (1/82), pp. 22-25 and unnumbered page.
*J. of Bone and Joint Surgery*, vol. 59-A, No. 1, Jan. 1977, pp. 77-79, Lotke, P. A. et al., "Influence of Positioning of Prosthesis in Total Knee Replacement".
2nd European Congress of Knee Surgery And Arthroscopy, Basel, Sep.-Oct. 1986, Abstract Book, Cooke, T. D. V. et al., "Application of Bench Mounted Saws for Precision Arthroplasty of the Arthritic Knee (Questor Knee Jigs)".
*J. Biomed. Eng.*, vol. 7, Jan. 1985, pp. 45-50, Cooke, T. D. V. et al., "Universal Bone Cutting Device for Precision Knee Replacement Arthroplasty & Osteotomy".

*Primary Examiner*—Robert A. Hafer
*Assistant Examiner*—Charles H. Sam
*Attorney, Agent, or Firm*—Fleit, Jacobson, Cohn, Price, Holman & Stern

[57] ABSTRACT

A reference system for the implantation of condylar total knee prostheses comprises a measuring rod (1) parallel to the longitudinal axis of the tibia (T) having at least two attachment arms (2) for lateral attachment to the outside of the tibia (T), a guide rail (9) connected to the measuring rod having a measuring scale (10) thereon and an adjustable measuring carriage (11) to which a cutting block (15) for performing the necessary osteotomies is affixed for movement in two directions so that cutting block can be displaced and fixed in such a way that by slots therein, the osteotomy can be carried out at the right place. For determining the position, there is attached to the measuring rod an alignment bar (20) which forms the continuation of the measuring rod toward the pelvis and has a length such that the end reaches to the pelvis. Disposed at the top of the alignment bar is a movable alignment element which can, for setting purposes, be moved along the alignment bar at right angles to the sagittal plane and fixed. By means of a specific point of reference on the pelvic bone, i.e., a screw in the spina iliaca anterior superior, the tibia can be brought into the correct position during the operation.

20 Claims, 5 Drawing Sheets

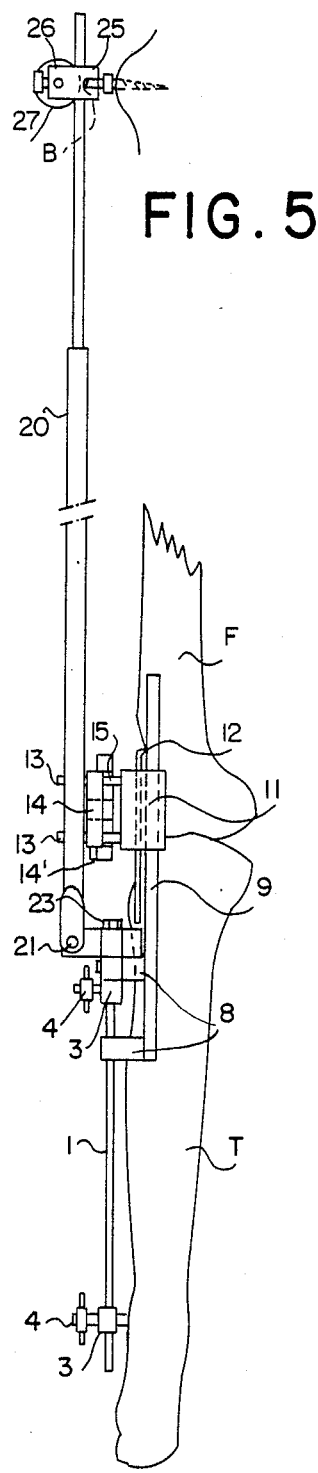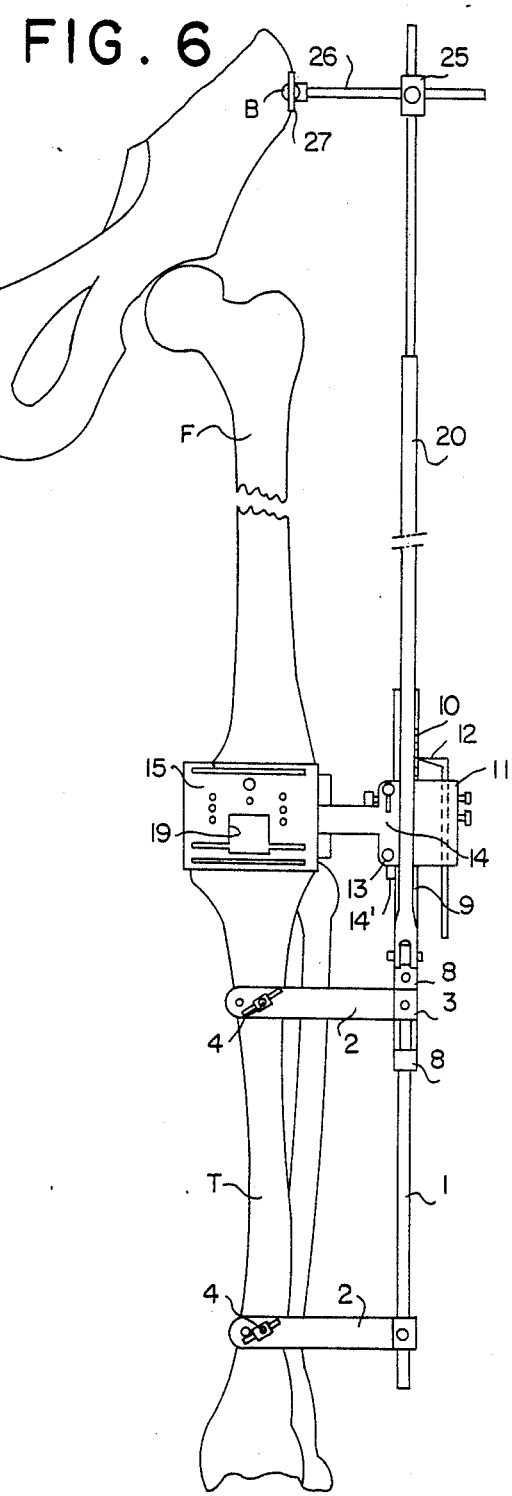

REFERENCE SYSTEM FOR IMPLANTATION OF CONDYLAR TOTAL KNEE PROSTHESES

BACKGROUND OF THE INVENTION

This invention relates to orthopedic replacement surgery, and more particularly to a reference system for the implantation of condylar total knee prostheses, a tenser for stretching the knee ligaments when the knee joint is flexed for producing a force between the femur and the tibia during an operation using the aforementioned reference system, a drilling template for making bores in the tibia for attaching such a reference system, and a procedure for carrying out exact osteotomies on the tibia and on the femur for the implantation of condylar total knee prostheses.

The inventive reference system enables the surgeon to perform the osteotomies extremely precisely. This is a prerequisite for being able to carry out the implantation in such a way that the correct mechanical axis of the leg is produced by means of the operation.

It has been demonstrated that achievement of the correct mechanical axis of the leg is one of the most important prerequisites for long life of the knee prosthesis without loosening and pain; cf. Bargren, J. H., et al., "Alignment in Total Knee Arthroplasty," Clinical Orthopaedics and Related Research, No. 173 (1983), pp. 178-183.

In this connection, it is not only a matter of bringing about the correct static knee structure (alignment), but it is likewise important for balanced tension of the knee ligaments to be present, insofar as they still exist, or the correct soft-tissue tension.

Condylar knee prostheses consist of a component fixed to the femur and a component fixed to the tibia. Unlike the hinge prosthesis, these components are not connected by artificial mechanical aids.

As in the natural knee joint, the flexible connection between the two components is made up of ligaments and muscles insofar as they are preserved during implantation of the prosthesis. Before the prosthesis components can be attached to the femur and the tibia by means of clamping, wedging, or bone cement, the femur and tibia must be shaped to fit the prosthesis with the aid of bone saws and other tools. The instruments generally offered by the manufacturers of the knee prostheses serve primarily to carry out the required matching bone cuts on the femur and the tibia, the osteotomies, with the necessary accuracy.

An essential requirement in this connection is that the components of the knee prosthesis which slide against one another when the knee is bent and straightened must always occupy correct relative positions, i.e., the mechanical axis of the leg must not deviate from the physiological axis of the leg by more than 3° varus or 3° valgus, and that correct tension of the various ligaments must be achieved, which produces good stability of the knee joint during both extension and flexion.

As a rule, the prior art instrumentaria for the implantation of condylar total knee prostheses comprise the following means:

means for aligning the tibia with the femur for attaining the desired leg-axis position;

means for carrying out osteotomies, in the form of cutting gauges serving to guide the saw; such cutting gauges are conformed to specific shapes of prostheses and can usually be used for various sizes of one type of prosthesis;

means for producing the desired tension of the knee ligaments.

Such instrumentaria are described, for example, in the following publications: "Immediate Interlock Without Cement—The TRICON-P TM Cementless Tibial Component with FLEX-LOX TM pegs," Memphis, Tenn., Richards Medical Company, 4/1983; Pappas, Michael J., et al., "N.J. Knee Instrumentation System: Biomechanical and Surgical Rationale," Bio-Medical Engineering Corp. Technical Report, 3,1983; "Surgical Technique Using AOR TM Total Knee Instrumentation for the Miller/Galante Porous Tivanium Total Knee System," Warsaw, Ind., Zimmer, undated (received 11/1986), pp. 8 & 18-20; "The Intermedics Natural-Knee TM System: Instrumentation," Austin, Tex., Intermedics Orthopedics, 2/1986; "Precise Bone Cuts ... Every Time—The Howmedical® Universal Total Knee Instrument System," Rutherford, N.J., Howmedica, Inc., 1980 (1/1982), pp. 22-25 and unnumbered page.

The prior art instrumentaria have the drawback that the cutting gauge for the osteotomies has two reference systems, viz., one on the tibia for cutting thereon, and a second one on the femur for cutting on that bone. For determining the cutting planes and for carrying out the osteotomy with the saw on the tibia, measuring means and cutting gauge are first attached to the tibia, e.g., by means of Steinmann's nails or bone-screws. After the tibia cut has been effected, the measuring means and cutting gauge are attached to the femur. During this changeover, an exact geometric relationship between the tibia-side and femur side components of the prosthesis is not ensured. Almost any surgeon who implants condylar total knee prostheses does, in fact, know of errors in this regard. Such errors are described, for instance, in Lotke, P. A. et al., "Influence of Positioning of Prosthesis in Total Knee Replacement," J. of Bone and Joint Surgery, No. 55-A (1977), pp. 77-79.

Steps have already been taken to avoid the aforementioned drawback, e.g., by fastening the knee to the operating table with a mechanical device, the saw also being connected to this device (cf. Cooke, T. D. V. et al., "Application of Bench-Mounted Saws for Precision Arthroplasty of the Arthritic Knee [Questor Knee Jigs]," Abstract Book, Second European Congress of Knee Surgery and Arthroscopy, Basel [Sept. 29-Oct. 4, 1986]; and J. Biomed. Eng., No. 7 [1985], pp. 45-50).

The devices described in the aforementioned publications comprise complicated mechanical structures which are time-consuming to use and also hamper access to the operating area.

BRIEF SUMMARY OF THE INVENTION

Consequently, it is an object of this invention to provide an instrumentarium which avoids the above described drawbacks of prior art instrumentaria.

A further object of the invention is to provide a reference system for the implantation of condylar total knee prostheses in which the measuring means and the cutting gauge for the tibial and femoral osteotomies are attached only to the tibia.

Still another object of the invention is to provide a reference system which can remain screwed to the tibia during the whole operation without significantly hindering access to the operating area and without preventing movement of the knee joint.

To this end, the reference system according to the present invention comprises a measuring rod having at least two attachment arms for attaching it laterally to the tibia, parallel to the longitudinal axis of the tibia, a guide rail of the measuring rod having a fixable measuring carriage which can be displaced longitudinally, the longitudinal position of which is exactly determinable by means of a longitudinal scale beside the knee to be operated on, to one side of the measuring carriage a removable cutting block as a gauge for the osteotomies being disposed in such a way that it can be brought into position in front of the knee, is movable on guide rods at right angles to the frontal plane and on the guide rail parallel to the longitudinal axis of the tibia, and can be fixed in the predetermined position, there being attached to the measuring rod an alignment bar which forms the continuation of the measuring rod in the direction of the pelvis and has a length such that its end reaches to the pelvis, there being disposed on the alignment bar at the top a movable sighting element which for adjustment can be moved along the alignment bar and at right angles to the sagittal plane and fixed so that, by means of a certain point of reference on the pelvic bone, the correct position of the lower leg can be adjusted or checked during the operation.

The tenser according to the present invention is of a tong-like design, having two movable parts connected by a pivot pin and capable of being precisely regulated and locked in the desired position by a means, the bent arm of one part being appliable to the roof of the intercondylar notch for exerting a force upon the femur, and the other part likewise having an arm which is, however, so designed that it can be braced on the upper modified Schanz screw which has already been driven in for fastening the lateral arm, the counterforce having to be taken up by the Schanz screw.

The drilling template according to the present invention consists of a flat rod having in the correct position holes for fastening the mounting arms of the measuring rod and in addition having a further hole by means of which the drilling template can be temporarily attached to the tibia by a nail.

The procedure for carrying out exact osteotomies according to the present invention, using the reference system defined above, comprises the steps of fastening the reference system in a lateral position to the tibia by the lateral fastening arms of the measuring rod by means of modified Schanz screws, inserting a screw as a point of reference for the osteotomies in the pelvic region, preferably on the spina iliaca anterior superior, adjusting the reference system mounted on the tibia by means of the aforementioned point of reference with the knee straightened, establishing the position of the cutting block as a gauge for the osteotomy on the head of the tibia, checking and if necessary correcting the rotation of the femur on the knee joint flexed at a 90° angle with ligaments stretched with the aid of the above tenser, carrying out the dorsal and ventral femur osteotomies on the flexed knee joint with the aid of the cutting block with a caliper bracket as gauge, the exact distance of the dorsal femur osteotomy from the tibia osteotomy being ensured, adjusting the correct ligament tension by means of the reference system, and carrying out the osteotomies of the distal femur by means of the cutting block moved into the correction position as a gauge, the tension of the ligaments being adjusted by means of a tenser.

The inventive reference system represents an instrumentarium by means of which the cutting gauge can be adjusted starting from the same point of reference for the tibial and femoral osteotomies. As stated above, the instrumentarium is preferably attached laterally to the tibia by two attachment arms by means of modified Schanz screws. The basic element of the instrumentarium is the measuring rod, which is attached by means of the attachment arms preferably about 10 cm. away from the axis of the tibia. Movably affixed to this measuring rod on the guide rail is the cutting block which can be moved precisely into position in front of the opened knee. Likewise disposed on the measuring rod is a so-called alignment bar which substantially represents the continuation of the measuring rod and reaches into the region of the pelvic bone. Prior to the operation, an alignment element, disposed displaceably relative to the alignment bar at the top thereof, is fixed, e.g., by a screw, in such a way that it is aimed at a certain point on the pelvic bone. This point is preferably a screw driven into the spina iliaca anterior superior perpendicular to the frontal plane. By means of the reference system, the tibia can be brought into the correct position relative to the femur at any time, even during the operation. This is particularly necessary when cutting has to be performed on the femur and, at a late stage of the operation, for correct insertion of the condylar total knee prosthesis.

At the location where it is connected to the measuring rod, the alignment bar preferably has a hinge allowing it to be swung away so that good accessibility to the operating area remains ensured. For the osteotomy of the ventral and dorsal femoral condyles, the knee is brought into flexed position. This position, too, is possible when using the reference system. If the osteotomy of the ventral and dorsal femoral condyles is performed in the first phase of the operation, the osteotomy of the tibia in the second phase, and the osteotomy of the distal condyles in the third phase, a tenser is inserted between the tibia and the femur before carrying out these second and third phases. In this state, the stretched ligaments and tissue pull the two bones together.

Hence auxiliary means are necessary for bringing the tibia into the correct position so that the osteotomies can be performed correctly on the tibia and femur with the joint flexed at 90° and on the femur with the leg extended. Such an auxiliary means is the tenser. Its task is to press the joint surfaces of the tibia and the femur apart, it being possible to check this action by means of the reference system.

Two different tensers are provided for, one for the osteotomies on the straightened knee, the other for osteotomies on the flexed knee.

The first tenser for the osteotomies on the straightened knee is preferably block-shaped device which be inserted between femur and tibia after the osteotomy on the head of the tibia has been carried out. The block is preferably so designed that on the top, two movable plates can be displaced toward the femur independently of one another, parallel to a plate lying on the tibia, e.g., by tightening screws, so that various spacings can be set between the medial and lateral femoral condyles and various forces exerted. In this way, it is possible to adjust the soft-tissue tension medially and laterally correctly and to check any axial correction possibly having to be made.

The second tenser is designed on the principle of expander-tongs and presents a number of advantages in conjunction with the inventive reference system as compared with prior art instruments of this kind. The tenser can be inserted when the knee is flexed without removing the cutting block. One arm of the tenser can be introduced through an aperture in such a way that it rests on the roof of the intercondylar notch. The other arm is formed so that it is braced against a bone screw driven into the tibia below the knee. This bone screw, a modified Schanz screw, has already been driven in for attaching the knee-side attachment arm. Bracing against this screw instead of against the tibia osteotomy adjacent to the femur has the advantage that the osteotomy surface is not damaged by the action of force. The tenser presents the further advantage that it is not hampered by the rotation of the knee joint caused by the medially and laterally differing soft-tissue forces, so that such rotation can be checked and modified as desired by known operative procedures.

If this position is correct, the measuring carriage with the cutting block can, with the aid of the scale on the guide rail, be moved into the proper position for the osteotomy of the distal condyles. At this time, the spacing of the cuts on the tibia and the femur is adapted to the prosthesis to be implanted. The inventive reference system is important not only for the osteotomies but also during implantation of the prosthesis components since their correct adaptation, including the proper axial relationships, can be checked at any time during this decisive phase of the operation.

The lateral placement of the reference system lessens parallax errors during checking of the axial position. Such parallax errors are greater with frontal alignment bars of conventional instrumentaria since the neutral rotation position of the extended leg cannot be reliably established during the operation owing to the covering of sterile cloths.

The correct leg-axis position with the knee joint straightened is checked by means of the alignment bar. For this purpose, the distance from the iliac spine to the center of the hip joint is measured pre-operatively on a pelvic survey radiograph and transferred at the distal end of the instrumentarium to the alignment element or iliac spine pointer.

The reference system is basically suitable for any desired sequence of osteotomies. This sequence is established by the operating surgeon according to the condition of the knee joint and the axial position present.

BRIEF DESCRIPTION OF THE DRAWINGS

A preferred embodiment of the invention will now be described in detail with reference to the accompanying drawings, wherein:

FIG. 5 is a side elevational view of the reference system;

FIG. 6 is a front elevational view of the reference system;

DETAILED DESCRIPTION

Figure 1:
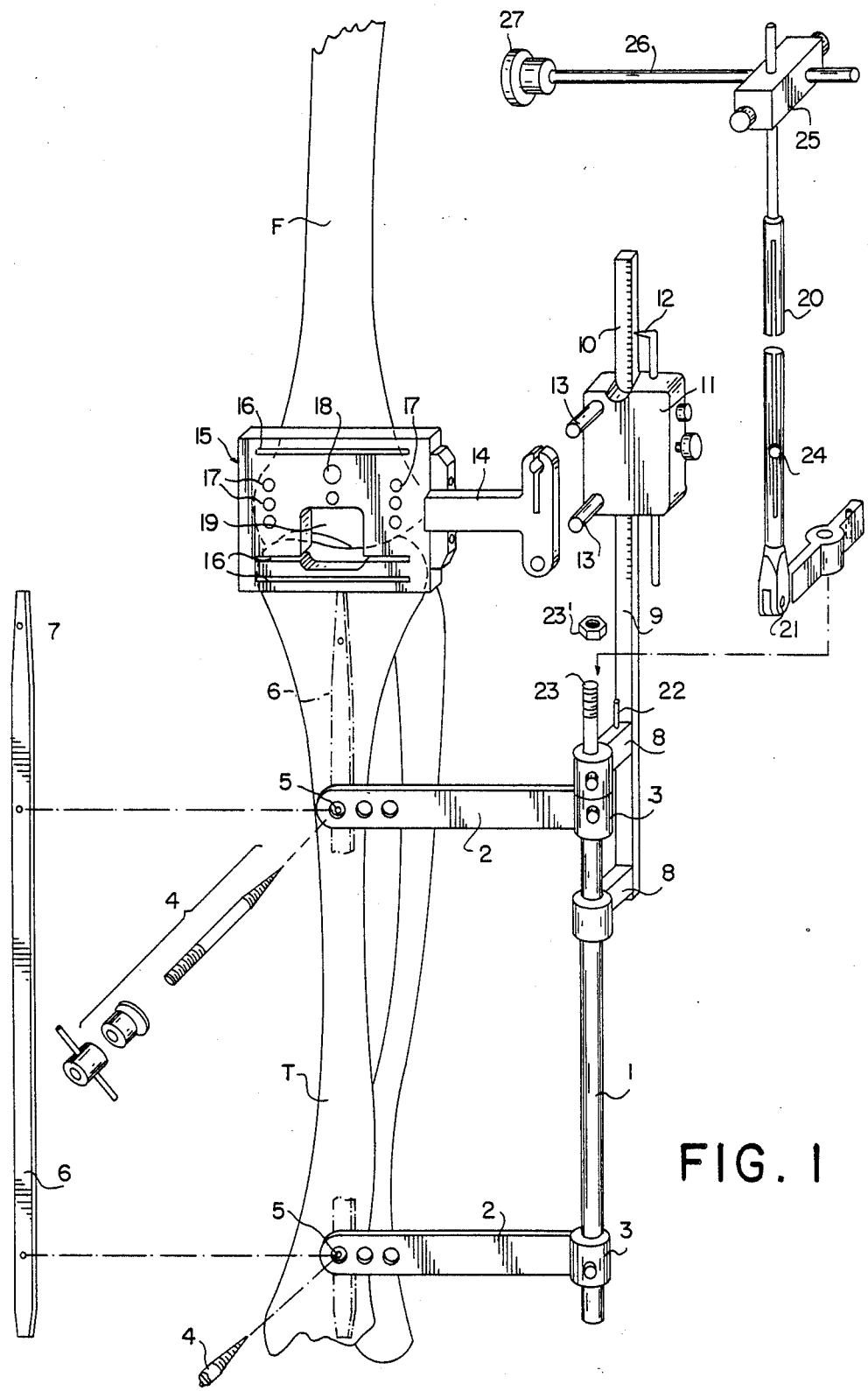
FIG. 1 is a perspective survey diagram of the reference system of the invention and of the portions of bone to which it is applied.

FIG. 1 shows in a survey view the instrumentarium which comprises the essential components of the inventive reference system. Also shown are a tibia T and a femur F to which the reference system is to be applied. Disposed on a measuring rod 1 are lateral attachment arms 2 which are connected to measuring rod 1 by attachment means 3. Measuring rod 1 is attached to tibia T by means of Schanz screws 4 passing through holes 5 in arms 2. Associated bores 5 for modified Schanz screws 4 are drilled in tibia T by means of a template 6 during the course of preparation for the operation, template 6 being fixed to the head of the tibia by a Steinmann's nail driven into the head through a bore 7.

Secured to measuring rod 1 by attachment means 8 is a guide rail 9 including a scale 10. Disposed on guide rail 9 is a measuring carriage 11 which can be slid in the region of scale 10 into the position necessary for the osteotomies. Alternatively, measuring rod 1 and guide rail 9 might be made in one piece. In the present embodiment, guide rail 9 is set back relative to the frontal plane so that the operating area is optimally liberated. Disposed on measuring carriage 11 is a movable pointer 12 by means of which the scale can be calibrated for each operation. Carriage 11 includes guide rods 13 for guiding a guide element 14 of a cutting block 15. Cutting block 15 can be displaced outwardly and inwardly in a direction normal to the frontal plane on guide rods 13 and fixed in position by suitable means such as set screw 14', for example. Cutting block 15 includes slots 16 for insertion of a sawing instrument and various holes 17 for receiving Steinmann's nails. A hole 18 is intended for attaching a caliper bracket (see FIG. 3) used for osteotomies on the femur with the knee in flexed position (cf. FIG. 2). An alignment bar 20 is removably fastened to a pin 22 and a threaded connecting portion 23 of measuring rod 1 by means of a hinge part 21. As illustrated in FIG. 1, it is shown detached. During the operation, alignment bar 20 can be swung away through 180° rotation about the hinge, thus allowing unhindered access to the operating area. In this embodiment, alignment bar 20 can be telescoped for easier handling and locked against rotation by a stud 24 entering a groove. An alignment element 26 is slidingly attached by means of a removable mounting 25 and can be fixed by tightening a screw on this mounting. Sighting element 26 ends in a knob 27 which can be aligned with the point of reference of the operation, viz., a screw B in the spina anterior superior of the pelvis (cf. FIGS. 5 and 6).

Figure 2:
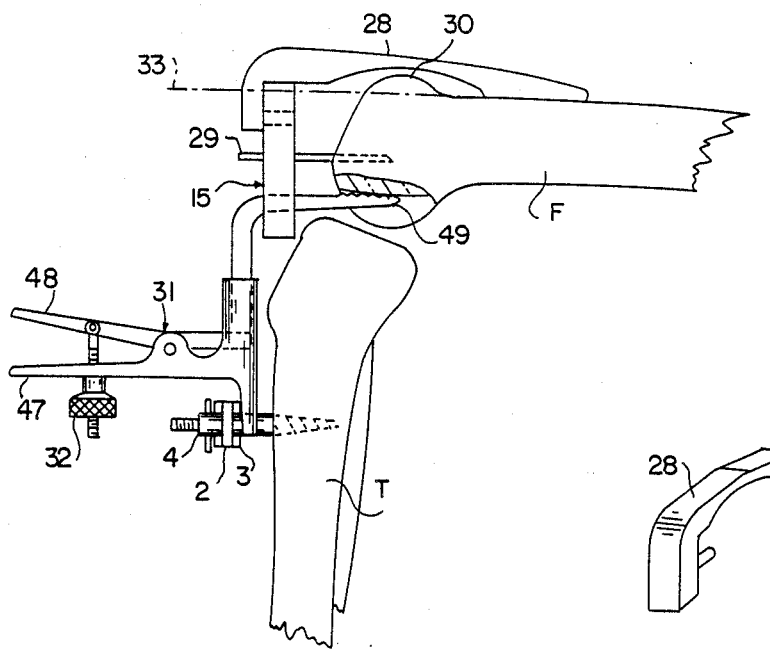
FIG. 2 is an elevational view of a knee joint to which the reference system is applied, flexed at a 90° angle and distracted with the aid of a tenser.
Figure 3:
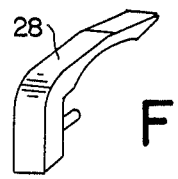
FIG. 3 is a perspective view of a caliper bracket.

In FIGS. 2 and 3, the position of cutting block 15, with caliper bracket 28 placed thereon, is shown relative to the flexed knee. Cutting block 15 is attached to femur F by two Steinmann's nails 29. Ventral condyles 30 are osteotomized through the uppermost saw slot 16, at which time the femur is pressed away from the tibia T by means of a tenser 31. An arm 49 of tenser 31 for flexed knee is inserted through an aperture 19 in cutting block 15. The arm of part 47 of tenser 31 is braced against the upper modified Schanz screw 4 in tibia T. A screw 32 fixes parts 47 and 48. The osteotomy 33 of the ventral femoral condyles is further indicated.

Figure 4:
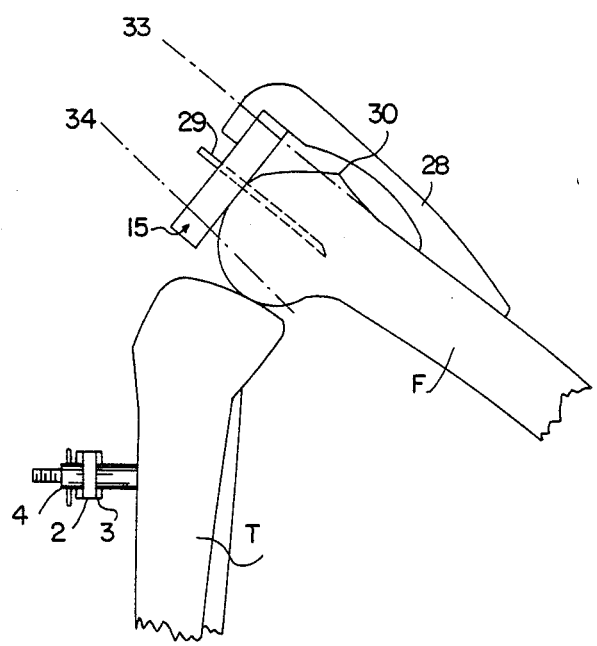
FIG. 4 is an elevational view of the flexed knee joint with cutting block and caliper bracket of the reference system, showing the osteotomies to be performed.

FIG. 3 shows caliper bracket 28 in perspective, while FIG. 4 indicates by means of a dot-dash cutting line 34 the position of the osteotomy of the dorsal condyles.

FIG. 5 is a side view of the reference system with the knee straightened. Here the attachment of measuring rod 1 to tibia T by means of Schanz screws 4 is apparent. In the present embodiment, guide rail 9, on which measuring carriage 11 is guided, is set back relative to the part of measuring rod 1 fastened to the tibia, thus affording better access to the operating area. Affixed to the set back part of measuring rod 1 is carriage 11, which includes movable pointer 12 for reading off scale 10. Guide rods 13, on which cutting block 15 is movably mounted by means of guide element 14, are attached to carriage 11. Alignment bar 20 is fastened to measuring rod 1 on threaded connecting portion 23 thereof; it can be swung back by means of hinge part 21 and, if necessary, removed by taking off a nut 23'. At the top of alignment bar 20 is mounting 25 by means of which alignment element 26 with palpation element 27 can be brought into the proper position.

FIG. 6 shows the same arrangement from the front. Here the lateral connection of measuring rod 1 by means of attachment arms 2 is clearly apparent, these arms being fixed to the tibia by Schanz screws 4. The position of cutting block 15 in front of the knee is also made plain. Guide rail 9 on which measuring carriage 11 slides is so disposed that cutting block 15 can be moved into the correct position for all the necessary cutting. Furthermore, the function of alignment bar 20 with alignment element 26 and palpation element 27 can be deduced. If, prior to the operation, the position of alignment element 26 on alignment bar 20 and the distance between palpation element 27 and alignment bar 20 are determined, the position of the tibia can be corrected at any time during the operation by resting palpation element 27 against a screw in the spina iliaca anterior superior as the point of reference. On guide element 14 a fixing screw 14' is disposed which allows guide element 14 carrying cutting block 15 to be fixed in a predetermined position.

Figure 7:
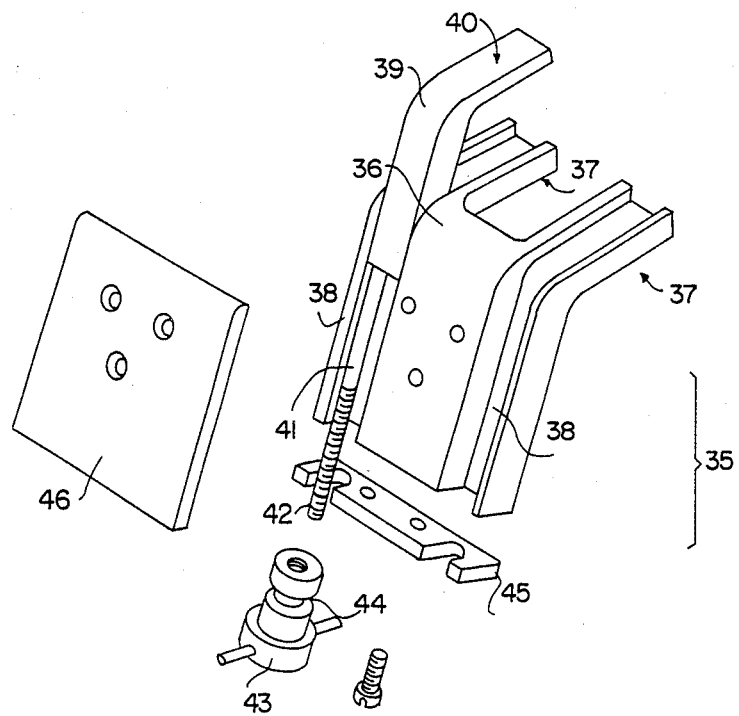
FIG. 7 is an exploded perspective view of a tenser for the straightened knee.
Figure 8:
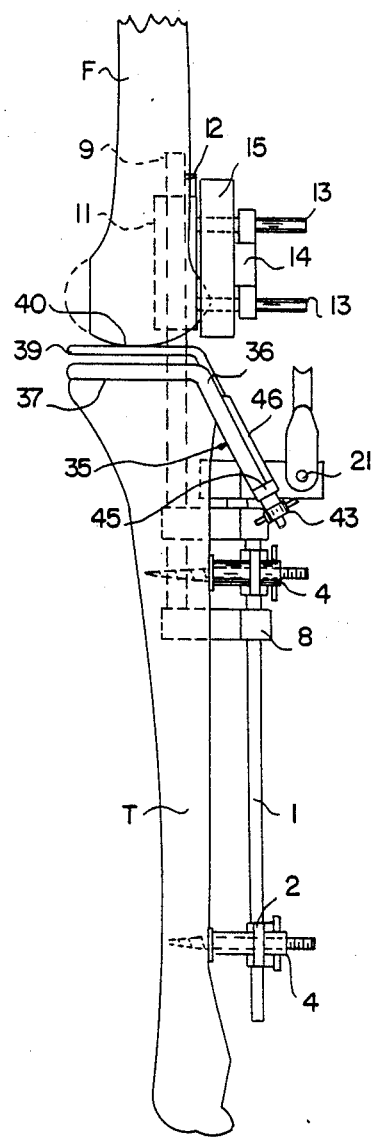
FIG. 8 is a side elevational view of the reference system, illustrating the effect of the first tenser on the straightened knee.

FIG. 7 shows a tenser 35, the application of which is further elucidated by FIG. 8. A part 36 includes support surfaces 37 for the osteotomized tibia. In guide grooves 38 there are parts 39 having support surfaces 40 for the femoral condyles. Disposed on each part 39 is a bolt 41 with a thread 42 at one end for receiving a nut 43 having a radial groove 44. Parts 39 and nuts 43 are held together on part 36 by a base plate 45 and a cover plate 46. Through this arrangement, parts 39 can be precisely moved relative to part 36 by turning nuts 43. Support surfaces 37 and 40 then remain parallel; only the spacing is changed.

FIG. 8 depicts the application of tenser 35 in conjunction with the reference system essentially as illustrated in FIG. 5, the difference being that here the osteotomy of the tibia and of the dorsal and ventral femoral condyles has already been carried out. The position of the instrumentarium corresponds to the preparation of the osteotomy of the distal femoral condyles. The tibia is pushed away from the femur by the pressure of support surfaces 37, 40. Once the correct position has been adjusted, cutting block 15 can be moved to the predetermined location and the osteotomy performed.

Figure 9:
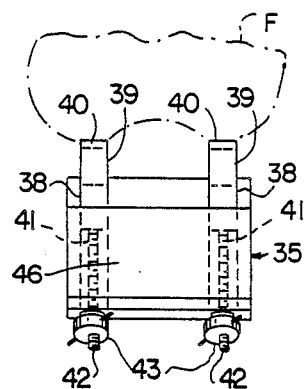
FIG. 9 is a front elevational view of the tenser for the straightened knee.

FIG. 9, shows tenser 35 from the front. Here it is particularly apparent how support surfaces 40 of movable parts 39 act upon the femoral condyles. It will be seen that by turning grooved nuts 43, the space between the tibia and femur can be increased or decreased. Downwardly directed part 36 with cover plate 46 affords optimum access to the operating area for carrying out osteotomies on the femur.

One advantage of the inventive instrumentarium is that the surgeon may perform the osteotomies in any desired order. In the case of a joint having a significantly immobilized false frontal position, he will first perform the osteotomy of the distal tibia and then correct the soft-tissue tension surgically. The osteotomy of the ventral and dorsal femoral condyles after correction of the ligaments then ensures a stable joint, both in extension and in flexion. In the case of joints with a largely correct axial position, osteotomy of the ventral and dorsal femoral condyles may be performed first.

When the cutting block is used in the flexed position of the knee, its position is determined by the Steinmann's nails and the caliper bracket. The osteotomy of the ventral condyles takes place through the uppermost sawing slot and that of the dorsal condyles through the middle sawing slot. The spacing of the bores in the cutting block for fixing by the Steinmann's nails corresponds to the various prosthesis sizes. The cutting block can be lifted off, displaced by the bore interval, and replaced on the two Steinmann's nails.

Inasmuch as the cutting block is additionally displaceable in sagittal direction at right angles to the measuring rod on guide rods of the measuring carriage, it can be moved into the optimum position for any osteotomy on the tibia and the femur.

The position of the cutting block can be determined, according to the size of the components of the prosthesis, from a table accompanying the instrumentarium.

As already pointed out, the correct leg-axis position with the knee straightened is checked using the alignment bar, the distance from the spina iliaca anterior superior to the center of the hip joint having been measured pre-operatively on a pelvic survey radiograph and transferred to the distal end of the alignment bar by means of the palpation element or iliac spine pointer.

The correct resection height is set on the measuring rod, and the cutting block is screwed to the osteotomized ventral condyles by a cortex screw having a diameter of 4.5 mm. The distal condyles are osteotomized through the lowest slot of the cutting block, the axial position being repeatedly checked with the alignment bar. For this procedure, continuous application of the tenser is prerequisite.

What is claimed is:

1. A reference system for the implantation of condylar total knee prostheses, comprising:
   a measuring rod;
   at least two attachment arms for attaching said measuring rod laterally to the tibia so that said measuring rod extends parallel to the longitudinal axis of the tibia;
   a guide rail on said measuring rod;
   an adjustable measuring carriage on said guide rail for displacement longitudinally thereon;
   longitudinal scale means for determining the longitudinal position of said measuring carriage relative to said guide rail;
   guide rods extending from said measuring carriage;
   cutting block means removably mounted on said guide rods for movement in a direction substantially perpendicular to the frontal plane of the knee for positioning said cutting block means in a predetermined fixed position in front of the knee so that said cutting block means functions as a gauge for osteotomies;

an alignment bar mounted on said measuring rod as a continuation of said measuring rod substantially in the direction of the pelvis and having a length sufficient to extend at least to a position adjacent the pelvis; and an alignment element adjustably mounted on said alignment bar for adjustment in a direction substantially perpendicular to the sagittal plane and relative to a predetermined reference point on the pelvic bone for determining the correct position of the lower leg during the operation.

2. The reference system as claimed in claim 1 wherein:

said attachment arms extend laterally from said measuring rod and have a length of 8 to 15 cm;

attachment means are provided on said attachment arms for rotatably and fixably mounting said arms on said measuring rod for rotation through substantially 180°; and a plurality of attachment bores are provided on each attachment arm for receiving special bone screws therethrough so that the spacing of the measuring rod from the tibia is adjustable for centering said cutting block in front of the intercondylar notch.

3. The reference system as claimed in claim 1 wherein:

said alignment bar is removably mounted on said measuring rod;

cooperating means are provided on said alignment bar and said guide rail for preventing relative rotation thereof; and hinge means is provided on said alignment bar to facilitate pivotal adjustment of said alignment bar in the sagittal plane.

4. The reference system as claimed in claim 1 wherein:

said measuring carriage further comprises an adjustable pointer cooperating with said scale means for calibrating the reference system.

5. The reference system as claimed in claim 1 wherein:

said guide rods comprise two guide rods extending in a direction substantially perpendicular to the frontal plane; and said cutting block means comprises a guide element adjustably and fixably mounted on said guide rods for displacement along said guide rods into a desired fixed position.

6. The reference system as claimed in claim 1 wherein:

a plurality of slots are provided in said cutting block means for use as template means for sawing instruments used in performing osteotomies.

7. The reference system as claimed in claim 6 and further comprising:

a tenser aperture in said cutting block means; and a tenser removably mounted on said reference system and extending through said tenser aperture for use on the knee in the flexed position without removing said cutting block means.

8. The reference system as claimed in claim 6 and further comprising:

a caliper bracket removably mounted on said cutting block means for positioning said cutting block means for defining a O-point as the point of reference for the osteotomies and for osteotomies of the neutral and dorsal femoral condyles.

9. The reference system as claimed in claim 1 wherein:

said alignment element comprises a rod shaped element having an outer end, a knob-shaped palpation element on said outer end for applying to the spina iliaca anterior superior, and means for detachably mounting said rod shaped element on said alignment bar.

10. The reference system as claimed in claim 1 wherein a tenser is provided for stretching knee ligaments when the knee joint is flexed to produce a force between the femur and tibia during an operation comprising:

a first part having a support arm engageable with a bone screw attaching one of said attaching arms to the tibia;

a second part movably supported on said first part and having a bent arm with an outer portion engageable with the roof of the intercondylar notch for exerting a force upon the femur;

a tong-like member pivotally connected to said first part and engaging said second part so that pivotal movement of said tong-like member moves said second part outwardly with respect to said first part for exerting said force on said femur; and regulator means between said tong-like member and said first part for precisely regulating the movement of said second part relative to said first part.

11. The reference system as claimed in claim 1 and further comprising:

a template in the shape of a flat rod;

holes in said attachment arms for attaching screws for attaching said attachment arms to the tibia;

holes in said flat rod a predetermined distance apart corresponding to the location of said holes in said attachment arms for locating the attaching screws in the tibia; and a further hole in said flat rod for a nail to temporarily attach said template in the correct position on the tibia to locate the attachment screws.

12. The reference system as claimed in claim 2 wherein:

said alignment bar is removably mounted on said measuring rod;

cooperating means are provided on said alignment bar and said guide rail for preventing relative rotation thereof; and hinge means is provided on said alignment bar to facilitate pivotal adjustment of said alignment bar in the sagittal plane.

13. The reference system as claimed in claim 12 wherein:

said measuring carriage further comprises an adjustable pointer cooperating with said scale means for calibrating the reference system.

14. The reference system as claimed in claim 13 wherein:

said guide rods comprise two guide rods extending in a direction substantially perpendicular to the frontal plane; and said cutting block means comprises a guide element adjustably and fixably mounted on said guide rods for displacement along said guide rods into a desired fixed position.

15. The reference system as claimed in claim 14 wherein:

a plurality of slots are provided in said cutting block means for use as template means for sawing instruments used in performing osteotomies.

16. The reference system as claimed in claim 15 and further comprising:
   a tenser aperture in said cutting block means; and
   a tenser removably mounted on said reference system and extending through said tenser aperture for use on the knee in the flexed position without removing said cutting block means.

17. The reference system as claimed in claim 10 and further comprising:
   a caliper bracket removably mounted on said cutting block means for positioning said cutting block means for defining a O-point as the point of reference for the osteotomies and for osteotomies of the neutral and dorsal femoral condyles.

18. The reference system as claimed in claim 16 wherein:
   said alignment element comprises a rod shaped element having an outer end, a knob-shaped palpation element on said outer end for applying to the spina iliaca anterior superior, and means for detachably mounting said rod shaped element on said alignment bar.

19. The reference system as claimed in claim 17 wherein:
   a tenser aperture is provided in said cutting block means;
   said bent arm extends through said tenser aperture in use; and
   a plurality of slots are provided in said cutting block means for use as a template means to guide sawing instruments used in performing osteotomies.

20. A method for performing osteotomies on the tibia and femur for implantation of condylar total knee prostheses using the reference system as claimed in claim 10 comprising:
   (a) fastening the reference system in a lateral position to the tibia by the attachment arms of the measuring rod by means of screws;
   (b) inserting a screw as a point of reference for the osteotomies in the pelvic region on the spina iliaca anterior superior;
   (c) adjusting the reference system mounted on the tibia by means of said point of reference with the knee straightened;
   (d) positioning the cutting block as a gauge for the osteotomy on the head of the tibia;
   (e) flexing the knee joint at a substantially 90° angle;
   (f) stretching the ligaments by operating the regulator means of the tenser to adjust the second part outwardly to move the femur away from the tibia;
   (g) checking and correcting the rotation of the femur on the knee joint while flexed with ligaments stretched with the aid of the tenser; and
   (h) performing dorsal and ventral femur osteotomies on the flexed knee joint with the aid of the cutting block means and caliper bracket as a gauge to ensure the exact distance of the dorsal femur osteotomy from the tibia osteotomy.

* * * * *